(12) United States Patent
Guerra

(10) Patent No.: US 10,888,465 B1
(45) Date of Patent: Jan. 12, 2021

(54) SURGICAL RECOVERY

(71) Applicant: Ariadna Guerra, Homestead, FL (US)

(72) Inventor: Ariadna Guerra, Homestead, FL (US)

(*) Notice: Subject to any disclaimer, the term of this patent is extended or adjusted under 35 U.S.C. 154(b) by 0 days.

(21) Appl. No.: 16/920,483

(22) Filed: Jul. 3, 2020

(51) Int. Cl.
*A61F 13/14* (2006.01)
*A61F 13/02* (2006.01)
*A61F 13/00* (2006.01)

(52) U.S. Cl.
CPC ........ *A61F 13/148* (2013.01); *A61F 13/0273* (2013.01); *A61F 2013/00089* (2013.01)

(58) Field of Classification Search
CPC .............. A61F 13/148; A61F 13/0273; A61F 2013/00089; A61F 13/14; A61F 13/02; A61F 2013/00361
USPC .......................................................... 602/61
See application file for complete search history.

(56) References Cited

U.S. PATENT DOCUMENTS

| 2017/0240777 A1* | 8/2017 | Proctor, Jr. ............ C09J 133/10 |
| 2017/0360867 A1* | 12/2017 | George ................. A61K 9/0021 |
| 2018/0104087 A1* | 4/2018 | Hietanen ................. A61H 23/02 |

FOREIGN PATENT DOCUMENTS

WO     WO-2017031567 A1 *   3/2017    ............ A61L 15/58

* cited by examiner

*Primary Examiner* — Tarla R Patel
(74) *Attorney, Agent, or Firm* — Christopher J. Vandam, PA; Chris Van Dam

(57) ABSTRACT

A surgical recovery process for improving the adhesion of the skin to substrate after procedures such as liposuction. A kinetic tape is adhered outside of the surgical area and then stretched along a midline of the abdomen over the rectus abdominis muscles and then adhered to the skin to pull the skin into a better position for healing. Additional segments of kinetic tape are similarly anchored to the skin outside of the surgical area to pull skin over the side muscles of the abdomen. The kinetic tape remains applied for a period of days and may optionally be reapplied to be continually refined the healing process.

7 Claims, 4 Drawing Sheets

SURGICAL RECOVERY

CROSS-REFERENCES TO RELATED APPLICATIONS

None.

STATEMENT REGARDING FEDERAL SPONSORED RESEARCH OR DEVELOPMENT

None.

NAMES OF PARTIES TO A JOINT RESEARCH AGREEMENT

None.

REFERENCE TO A "SEQUENCE LISTING", A TABLE, OR A COMPUTER PROGRAM LISTING APPENDIX SUBMITTED ON COMPACT DISC AND INCORPORATION-BY-REFERENCE OF THE MATERIAL ON THE COMPACT DISCLOSURE

None.

STATEMENT REGARDING PRIOR DISCLOSURES BY AN INVENTOR OR JOINT INVENTOR

None.

BACKGROUND OF THE INVENTION

1. Field of the Invention

The present invention relates to recovering from surgical procedures, and more particularly, to an improved method with associated devices to aid in post-surgical therapeutic recovery.

2. Description of Related Art Including Information Disclosed Under 37 CFR 1.97 and 37 CFR 1.98

Several methods for surgical recovery have been designed in the past. None of them, however, includes the use of kinetic tape anatomically applied aligned with underlying musculature used with therapeutic manipulation that expresses fluids to aid reattachment of integument to underlying substrate.

Applicant believes that the closest reference corresponds to widely used compression bandages, taping and suturing surgical wounds. However, it differs from the present invention because none of the prior art is able to hold the integument aligned with the musculature post-surgery to avoid wrinkling, misalignment, folds, flaps and recovery delays associated with surgeries.

Other patents describing the closest subject matter provide for a number of more or less complicated features that fail to solve the problem in an efficient and economical way. None of these patents suggest the novel features of the present invention.

A brief abstract of the technical disclosure in the specification and title are provided as well for the purposes of complying with 37 CFR 1.72 and are not intended to be used for interpreting or limiting the scope of the claims.

Without limiting the scope of the invention, a brief summary of some of the claimed embodiments of the invention is set forth below. Additional details of the summarized embodiments of the invention and/or additional embodiments of the invention may be found in the detailed description of the invention below.

BRIEF SUMMARY OF THE INVENTION

It is one of the main object of the present invention to provide a surgical recovery method and associated devices to reduce the recovery time and associated patient suffering.

It is another object of the invention to provide a means to aid in surgical recovery by ensuring proper anatomical alignment of the integument with underlying substrate through the recovery process.

It is yet another object of the present invention to reduce the need for subsequent corrective surgeries after a primary surgical event.

It is yet another object of this invention to provide such a process with associated devices that is inexpensive to manufacture and maintain while retaining its effectiveness.

Further objects of the invention will be brought out in the following part of the specification, wherein detailed description is for the purpose of fully disclosing the invention without placing limitations thereon.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE SEVERAL VIEWS OF THE DRAWING

With the above and other related objects in view, the invention exists in the details of construction and combination of parts as will be more fully understood from the following description, when read in conjunction with the accompanying drawings in which.

DETAILED DESCRIPTION OF THE INVENTION

Figure 1:
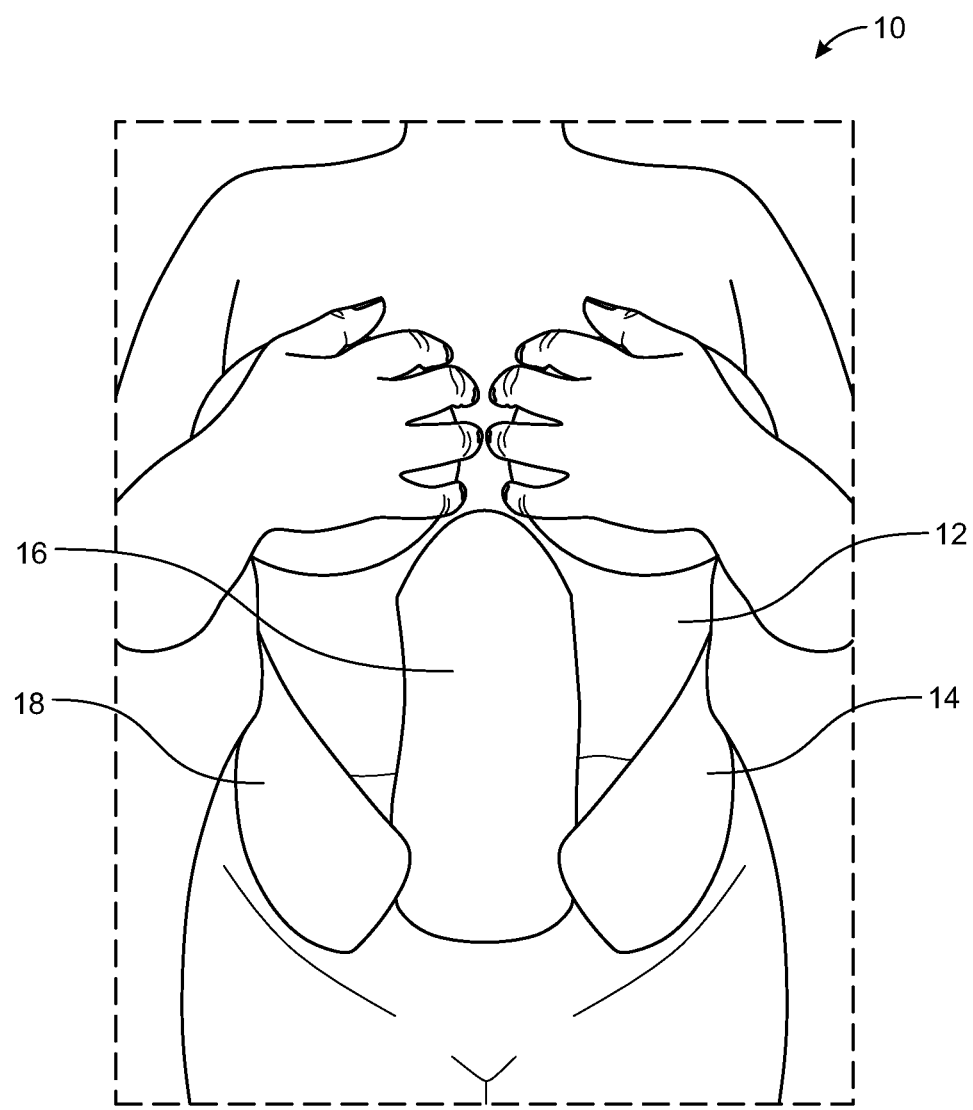
FIG. 1 shows a front elevation view of an example of kinetic bandage placement post surgery.

While this invention may be embodied in many different forms, there are described in detail herein specific embodiments of the invention. This description is exemplary of the principles of the invention and is not intended to limit the invention to the particular embodiments illustrated and described.

For the purpose of this disclosure, like reference numerals in the figures shall refer to like features unless otherwise indicated or is obvious by context.

The subject process with associated devices is sometimes referred to as the device, the invention, the surgical recovery method, rehabilitation process, the process, the method or other similar terms. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation.

Prior art post surgical therapeutic techniques have included bandaging for many years. More recently, massage techniques have also been introduced into a recovery regimen to aid in expression of built up bodily fluids between the underlying muscular substrate and the skin.

For example, in a cosmetic liposuction surgery the adipose tissue is removed separating the integument from the underlying musculature. Although this surgery is commonly well-tolerated this, like any surgery, creates wounds to tissues that undergo a healing process during the recovery. This rehabilitation process is generally monitored closely by members of the surgical team and therapists.

Prior art processes have used tapes over top of surgical incisions and sutures to hold the skin in position for several days to several weeks after the completion of the surgery. However, these can often lead to the skin reattaching to the underlying substrate in unpredictable and cosmetically undesirable ways. For example, immediately after surgery with a little connection between the integument and musculature the skin may tend to shift, slide, bunch and wrinkle as the patient moves throughout the healing process.

Kinetic tape is a product that has been used in sports medicine in the past. It has as a major component a stretchable structural fabric coated on one side with an adhesive. It is sometimes produced in sheets or in rolls. It has been used as a compression bandage in sports medicine. However, it has previously not been applied to surgical recovery procedures to realign and attach integument and musculature.

A superior surgical recovery result can occur when the skin is held in a precise position over the musculature to ensure that the skin attaches in the precise location desired by the surgical team. To achieve this the anatomy of the muscles and the orientation of muscle fibers is important to understand and implement in a post surgical bandaging regimen. Simply taping up the patient and sending them home often has unintended cosmetic consequences as the skin may shift.

The present method and associated kinetic taping improve the current state-of-the-art by providing a predictable and repeatable post-surgical recovery means by recognizing that the orientation of force provided by the kinetic tape on the integument is aligned to the orientation of the fibers in the muscle that contract when the patient is moving during the recovery process.

Figure 4:
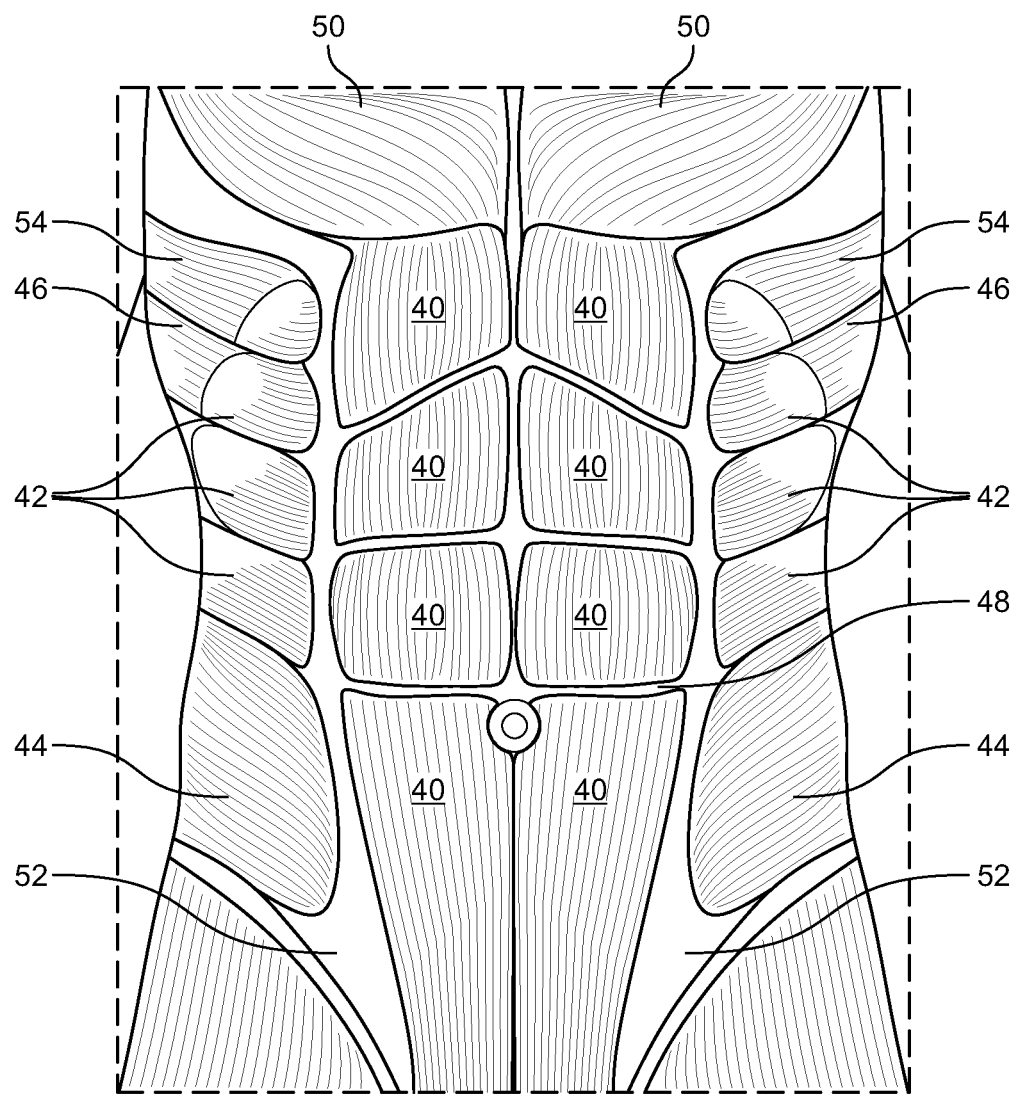
FIG. 4 is a front of elevation view demonstrating abdominal musculature anatomy and muscle fiber orientation.

Referring now to the drawings, where the present invention is generally referred to with numeral 10, it can be observed that it basically includes an abdomen 12 and several configurations of tapes 14-38. FIG. 4 demonstrates the abdominal musculature and includes, among other features, rectus abdominis 40, abdominal oblique 42, transversus abdominis 44, latissimus dorsi 46, tendinous inscription 48, pectoralis major 50, aponeurosis 52, and serratus 54.

Figure 2:
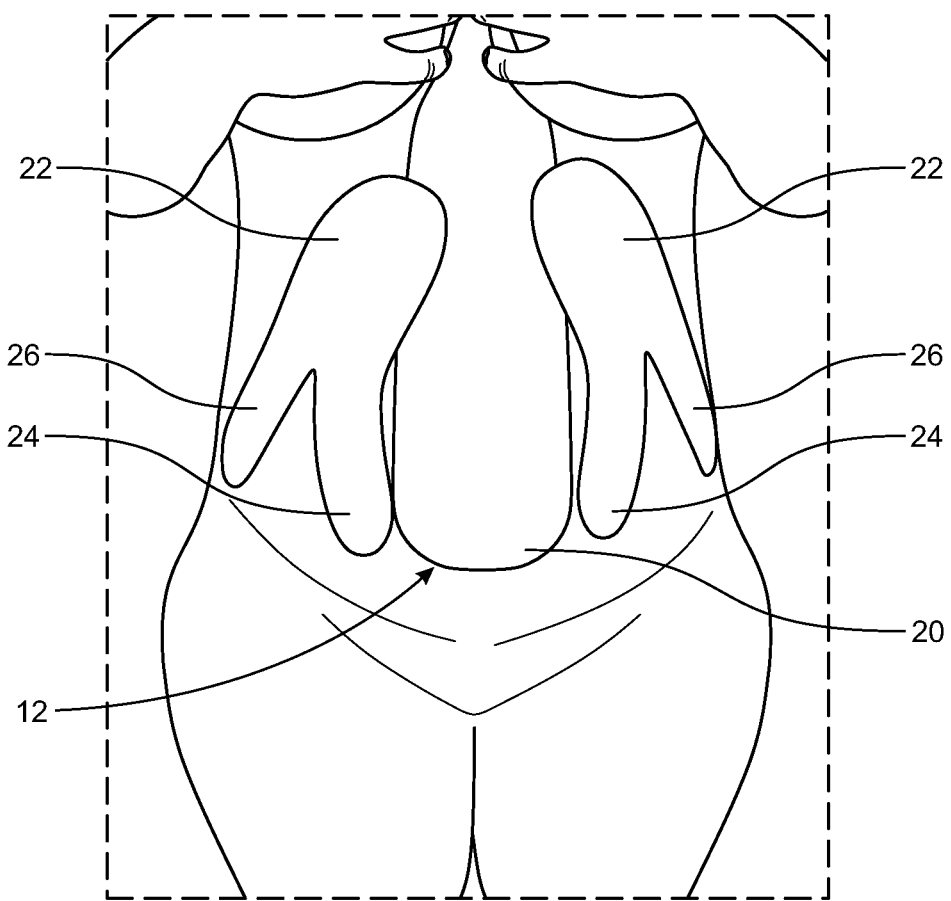
FIG. 2 shows a front elevation view of another example of kinetic bandage placement post surgery.
Figure 3:
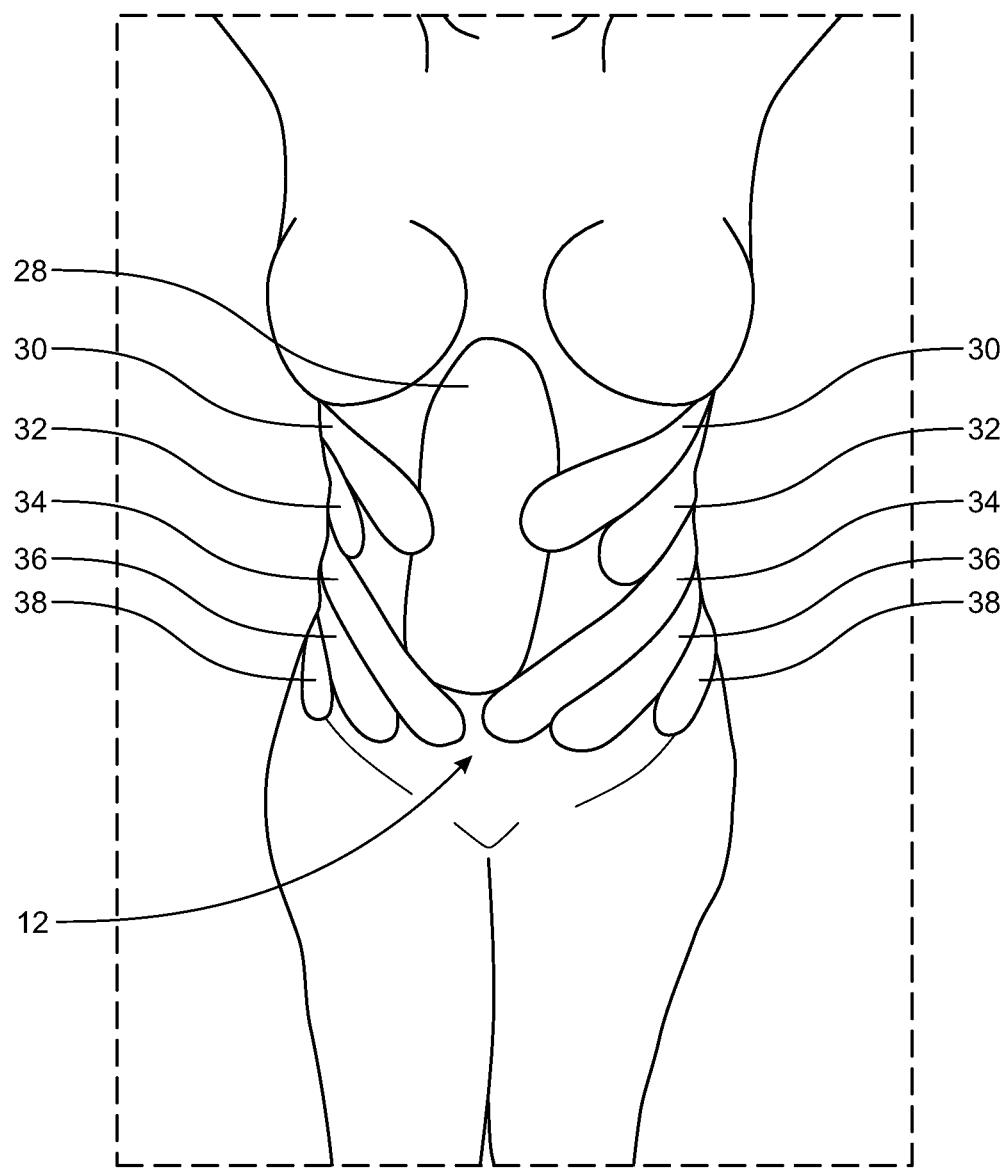
FIG. 3 shows a front elevation view of another example of kinetic bandage placement post surgery.

FIG. 4 showing the underlying musculature should be read in combination with the front elevation views of a patient undergoing treatment shown in FIGS. 1 through 3. Each of the FIGS. 1 through 3 show variations of tape usage for recovery for various abdominal surgeries. Although the figures demonstrate use on a female patient, the underlying musculature in males is similar and similar recovery principles are equally applied to men. Kinetic tape is sometimes referred to as tape in this specification.

After a cosmetic surgery, patients generally need a series of therapeutic massages to express fluid built up in the surgical area to aid in recovery. About two or three days after the surgery, and after several massages, the therapist precisely applies kinetic tape to the outer skin closely complementing the underlying musculature and the orientation of those muscle fibers.

In order to practice the procedure effectively the therapist must have an intimate knowledge of the anatomical musculature underlying the surgical event. Because the skin may be detached from the underlying substrate during a surgery, for example liposuction, the skin must be held in place during the recovery process. As the body heals from the trauma of surgery the skin will reattach to the underlying tissue.

If the recovery is not done correctly, the skin the may bunch or sag resulting in the need for an additional surgery to correct the situation, such as a tummy tuck. When the recovery treatments are done correctly the skin lines up appropriately and is held in place during the recovery period of approximately five to fourteen days.

The kinetic tape is applied to the skin and remains in place for several days. Five to fourteen days is a typical treatment time to allow the skin to reattach sufficiently to the underlying musculature. When the kinetic tape is to be removed the technician applies mineral oil or isopropyl alcohol, with or without heat, to generally loosen the adhesive on the rear of the kinetic tape. The technician takes care to avoid pulling the tape and risking detaching the healing skin.

After removal of the kinetic tape the skin continues to heal and retracts back into place. The process may be repeated several times of kinetic bandaging, removal and reapplication of kinetic bandages over the course of months. First beneficial results are noticeable in about four to six weeks in many patients. Patients are fully healed generally in about six months after the surgery. Individual patients recovery times will vary widely. It is important that the patient continues to seek the evaluation and treatment of the therapist to ensure that the recovery is progressing appropriately.

The recovery procedure can also be used for post childbirth abdominal diastasis recti. Diastasis recti can sometime occur post childbirth where muscles in the abdominal wall lose their shape pull apart and may separate. This condition is particular to the rectus abdominis 40 muscles (the six-pack muscles) in the abdomen.

The kinetic tape recovery procedure can be used post childbirth to reorient and tighten the muscle configuration of the rectus abdominis 40 while the patient is recovering from the delivery. Similar to the liposuction example above, holding the musculature in place during the healing process can ensure that appropriate anatomical configuration is retained as the patient moves.

Looking now at FIG. 1, a post liposuction kinetic tape configuration is demonstrated. The skin over the abdomen 12 is not firmly connected to the underlying musculature post-surgery. After the procedure for a couple of days, therapeutic massages are used to reduce the fluid build up. The image in FIG. 1 demonstrates the configuration of the kinetic tapes 14, 16 and 18 applied a couple of days after the surgery.

The tape 16 at one end is first affixed to the abdomen 12 by the adhesive integral to the kinetic tape 16. The kinetic tape 16 is stretched longitudinally over the rectus abdominis 40 muscles and then adhered along the entire length of the kinetic tape 16 to the integument of the abdomen 12. Similarly, the lateral edge of the tapes 14 and 18 are adhered to the patient's side. Then the kinetic tapes 14 and 18 are stretched and adhered along the length of the transversus abdominis 44 following the orientation of the muscle fibers.

It should be noted that the longitudinal axis of the kinetic tapes 14 and 18 are aligned with the muscle fibers of the transversus abdominis 44. Whereas, the tape 16 has a longitudinal stretching axis that parallels the muscle fibers of the rectus abdominis 40 muscles. Notice also that the ends of the kinetic tapes 14 and 18 are adhered to the lower edge of the kinetic tape 16 to tie all the taping together.

In this configuration, the skin that was detached from the underlying substrate through the liposuction surgery is held in place where that skin was attached prior to the surgery. The skin can then heal in the correct orientation and end up attached to the underlying musculature with little or no sagging. Minimal sagging or wrinkling will naturally correct itself over time by a natural tightening of the skin. Whereas, without this corrective kinetic taping procedure the skin may slide causing significant pockets or folds that would require a corrective procedure, such as a tummy tuck.

In the post-liposuction surgery treatment shown in FIG. 1 the upper end of the kinetic tape 16 is adhered to an anchor point of the pectoralis major 50 muscles and the uppermost rectus abdominis 40 that remains attached to the skin outside of the area of surgical intervention. The elastic nature of the kinetic tape 16 along with the longitudinal stretch induced to the tape 16 as it was applied to the abdomen 14 tends to lift and support the skin of the abdomen 12 during the healing and reattachment while allowing the patient to move during recuperation.

Similarly, the lateral aspects of the tape 14 and 18 are anchored on the side of the patient where the skin was not detached during the procedure. Also, on the medial side it attaches to the central kinetic tape 16. The retracting scratchiness of the kinetic tapes 14 and 16 both pull the skin and compress the wound ensuring complete contact of the integument to the underlying substrate as well as supporting the integument into the correct position.

Looking now at FIG. 2 another example of kinetic taping post surgery is demonstrated. The therapist or technician applying the kinetic tapes 20, 22, 24 and 26 must appreciate the nature of the surgery and they specific locations in the abdomen 12 where the skin is not firmly attached to the underlying musculature. The location of the tapes 22, 24 and 26 are also dependent in part on the body shape of the patient as well as the extent of the surgery.

The tape 20 is first adhered on the upper end over the sternum near the pectoralis major 50 muscles to anchor it. The tape 20 is then stretched and adhered over the skin of the abdomen 12 to pull the skin into place. The tape 22 is first split on a lower edge to create sub-tapes 24 and 26. By this means the orientation of the pulling caused by the stretch of the kinetic tape can be directed in multiple directions simultaneously to properly hold the skin in place.

The tape 22 is adhered in part over the edge of the previously secured tape 20. The portion of tape 26 is stretched laterally around the side of the abdomen 12 to pull the skin along the axis created from the length of tape 22 and 26. These tapes may be aligned perpendicular, parallel to or askew to the muscle fibers that underlying, including the transversus abdominis 44 and the abdominal obliques 42.

Similarly, the segment of tape 24 is stretched and adhered to a medial segment of the abdomen overlying the rectus abdominis muscles 42 to draw the skin in line with the fibers of the rectus abdominis 40 and the tendinous inscription 48. The segment of the tape 22 may be stretched perpendicular to the long axes of the tape to pull the skin over the serratus muscle 54.

Looking at FIG. 3, yet another variation of the recovery process is shown with a plurality of tapes 28, 30, 32, 34, 36 and 38 over the abdomen 12. Like the other procedures, the initial kinetic tape 28 is first applied near an anchor point along the pectoralis major 50 and stretched over the skin vertically over the media line of the abdomen 12 and then adhered to the skin while stretched to draw up the skin and prevent gravity from causing sags and dislocation of the skin from its natural position over the musculature below.

The series of tapes 30, 32, 34, 36 and 38 are stretched and adhered around the side aspects of the patient. The dorsal ends of these tapes 30-38 are initially adhered over an area of skin undisturbed by the surgical process. The tape 30 is pulled along the orientation of the serratus 54 muscle fibers and the ventral and adhered over the tape 28. The tape 32 is stretched over the latissimus dorsi 46 along its muscle fiber. The tapes 34 and 36 pull along the orientation of muscle fibers for the abdominal oblique muscles 42. The lowest tape 38 poles the skin from the middle toward the side of the patient along the transversus abdominis muscle 44.

By using the combination of tapes 28, 30, 32, 34, 36 and 38 these individual tapes are able to align the skin over individual muscles or closely located muscle groups. It is therefore essential that the technician applying these tapes is intimate with the knowledge of the underlying muscle structure and the orientation of those muscle fibers. The technician must also know which skin is undisturbed and which areas may provide a good anchor point for stretching the tapes.

Before the therapist applies any of the tapes they determine the location of the surgical procedure and the anatomy potentially damaged by the surgery. The therapist 12 pre-cuts segments of the tape. If the tape is segmented into multiple sections such as the tapes 22, 24 and 26 shown in FIG. 2, those cuts are made to configure the tapes prior to adhesion to the patient.

Any corners of the segments of tape are rounded to prevent the tape from premature pick up or coming loose from the skin. The backing protecting the adhesive side of the kinetic tape is removed, the tape is stretched and adhered to the patient. In some cases the protective backing from the adhesive is only partially removed while the anchor end of the tape is secured to the body and then the backing is removed as the tape is stretched in the proper position and gently pressed of the body to adhere the tape to the patient's skin.

In the one or two days after the surgery the patient' is typically very sensitive. Minimal massage is then provided prior to taping up to release any built up fluid. The tape is then applied and is warn for between about five and fourteen days. During the time the tape is on the patient they may be dry massaged gently so as to not interfere with the healing process where the skin reattaches to the underlying substrate. In some cases, after the tape is removed and the patient is reevaluated, a subsequent tape job is then applied for another approximately five to ten days. In some cases this reapplication of tape process can occur for six to ten cycles over the course of several months for a complete course of recovery treatment.

An important version of the invention can be fairly described as a surgical recovery process comprised of the steps of completing a surgical procedure (such as liposuction) during which an area of skin is detached from the substrate (underlying adipose, muscle and associated tissue. Then, massaging the area of skin for one to two days (maybe more depending on the procedure) after the surgical procedure to express fluid from the surgical site. Then, assessing a muscular aspect of the substrate to determine a location of a muscle and an orientation of a fiber of the muscle relative to the surgical site and wound. Then, preparing a kinetic (stretchy adhesive) tape to cover a section of the area of skin by cutting to shape and size. Then, adhering a first end of the kinetic tape adjacent to the area of skin at or near the edges of the surgical wound. Then, stretching the kinetic tape over the area of skin and attaching the entire kinetic tape to the area of skin to pull the area of skin into a proper position to allow the area of skin to reattach to the substrate during a healing process. Optionally, the first end of the kinetic tape is adhered immediately superior to the area of skin and over a pectoralis major muscle to anchor the first end of the kinetic tape in an area not detached from the substrate during the surgical procedure. Optionally, a second kinetic tape is adhered immediately lateral to the area of skin and is stretched over and then adhered to the area of skin to pull the area of skin into the proper position to allow the area of skin to reattach to the substrate during the healing process. The orientation of this second tape may best be aligned with the muscle fiber of the substrate or may be adapted to compensate for sagging skin to allow it to heal evenly and naturally thereby reducing the need for a later tummy tuck to remove the sags. Optionally, the kinetic tape is removed after five to fourteen days and the kinetic taping process described above is repeated.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

I claim:

1. A surgical recovery process comprised of the steps:
   completing a surgical procedure during which an area of skin is detached from an underlying substrate;
   massaging the area of skin for one to two days after the surgical procedure to express fluid;
   assessing a muscular aspect of the underlying substrate to determine a location of a muscle and an orientation of a fiber of the muscle;
   preparing a kinetic tape to cover a section of the area of skin;
   adhering a first end of the kinetic tape adjacent to the area of skin;
   stretching the kinetic tape over the area of skin; and
   attaching the entire kinetic tape to the area of skin to pull the area of skin into a proper position to allow the area of skin to reattach to the underlying substrate during a healing process.

2. The surgical recovery process of claim 1 further characterized in that the first end of the kinetic tape is adhered immediately superior to the area of skin and over a pectoralis major muscle to anchor the first end of the kinetic tape in an area not detached from the underlying substrate.

3. The surgical recovery process of claim 2 further characterized in that a second kinetic tape is adhered immediately lateral to the area of skin and is stretched over and then adhered to the area of skin to pull the area of skin into the proper position to allow the area of skin to reattach to the underlying substrate during the healing process.

4. The surgical recovery process of claim 3 further characterized in that the kinetic tape is removed after five to fourteen days and the process of claim 1 is repeated.

5. The surgical recovery process of claim 2 further characterized in that the kinetic tape is removed after five to fourteen days and the process of claim 1 is repeated.

6. The surgical recovery process of claim 1 further characterized in that a second kinetic tape is adhered immediately lateral to the area of skin and is stretched over and then adhered to the area of skin to pull the area of skin into the proper position to allow the area of skin to reattach to the underlying substrate during the healing process.

7. The surgical recovery process of claim 1 further characterized in that the kinetic tape is removed after five to fourteen days and the process of claim 1 is repeated.

* * * * *